(12) United States Patent

Kaarakainen et al.

(10) Patent No.: US 6,520,313 B1
(45) Date of Patent: Feb. 18, 2003

(54) ARRANGEMENT AND METHOD FOR HANDLING TEST TUBES IN A LABORATORY

(75) Inventors: Keijo Kaarakainen, Järvenpää (FI); Juha Korhonen, Espoo (FI); Ville Mäkelä, Vantaa (FI)

(73) Assignee: Thermo Clinical Labsystems Oy, Vantaa (FI)

( * ) Notice: Subject to any disclaimer, the term of this patent is extended or adjusted under 35 U.S.C. 154(b) by 0 days.

(21) Appl. No.: 09/712,257

(22) Filed: Nov. 15, 2000

(30) Foreign Application Priority Data

Nov. 15, 1999 (FI) .............................. 19992451

(51) Int. Cl.⁷ ............................... B65G 47/10
(52) U.S. Cl. ................ 198/369.5; 198/358; 198/370.1; 198/457.01
(58) Field of Search .......................... 198/369.5, 370.1, 198/358, 369.1, 457.01, 457.05

(56) References Cited

U.S. PATENT DOCUMENTS 3,193,087 A * 7/1965 Hahn ...................... 198/369.5
3,844,662 A 10/1974 Froreich (List continued on next page.)

FOREIGN PATENT DOCUMENTS

| DE | 2134884 | 2/1973 |
| DE | 2945524 | 5/1981 |
| DE | 3116926 | 11/1982 |
| DE | 4434714 | 4/1996 |
| DE | 19621179 | 11/1997 |
| EP | 0704391 | 3/1996 |
| EP | 732077 | 9/1996 |
| EP | 759406 | 2/1997 |
| EP | 775650 | 5/1997 |
| EP | 0856736 | 5/1998 |
| FI | 97913 | 4/1993 |
| GB | 2189884 | 11/1987 |
| JP | 63271164 | 11/1988 |
| JP | 9033539 | 2/1997 |

OTHER PUBLICATIONS

"Konelab 30, The Wizard of Analysis" Brochure, Konelab Intelligent Diagnostic Systems.

*Primary Examiner*—Douglas Hess
(74) *Attorney, Agent, or Firm*—Birch, Stewart, Kolasch & Birch, LLP

(57) ABSTRACT

The invention relates to an arrangement and method for transporting test tubes (1) automatically between different processing stages and equipment in laboratories. In the method, the test tubes (1) are placed on transport bases (3) for transportation within the system and the identification data of the test tube (1) is read to identify the sample, after which the transport bases (3) can be moved within the transportation system with the aid of conveyors (15–18)to operation stations, for operations to be carried out on the test tube (1) or sample. The data.required to move the transport base within the system are recorded in a memory circuit forming part of the transport base (3) on the basis of the identification data of the sample, which can be read without physical contact by a recording device (4), while the transport base (3) is handled at a control station (25), which is formed by at least one processing point together with the track (28) and which control station includes at least a handling device (36), in which there is a grip (38) which grips the transport base (3) and transfers the base (3) in a direction transverse to the direction of movement of the conveyor track, to take the transport base (3) to the processing point following the first processing point, and devices (37) which prevent the next transport base (3) from entering the control station (25) during the transfer, the data in the recording devices of the transport base (3) being read at the control station during handling.

11 Claims, 5 Drawing Sheets

U.S. PATENT DOCUMENTS

| | | | |
|---|---|---|---|
| 3,860,107 A | * | 1/1975 | Cioni et al. ................. 198/131 |
| 4,349,097 A | * | 9/1982 | Curti ....................... 198/369.5 |
| 4,461,836 A | | 7/1984 | Von Froreich |
| 5,078,257 A | * | 1/1992 | Carter, Jr. ................ 298/369.5 |
| 5,370,215 A | | 12/1994 | Markin et al. |
| 5,605,218 A | | 2/1997 | Von Froreich |
| 5,623,415 A | * | 4/1997 | O'Bryan et al. ............. 198/617 |
| 5,657,856 A | | 8/1997 | Von Froreich |
| 5,658,532 A | * | 8/1997 | Kurosaki et al. .............. 422/64 |
| 5,941,366 A | * | 8/1999 | Quinlan et al. .......... 198/465.1 |
| 6,343,690 B1 | * | 2/2002 | Britton et al. ......... 198/867.06 |

* cited by examiner

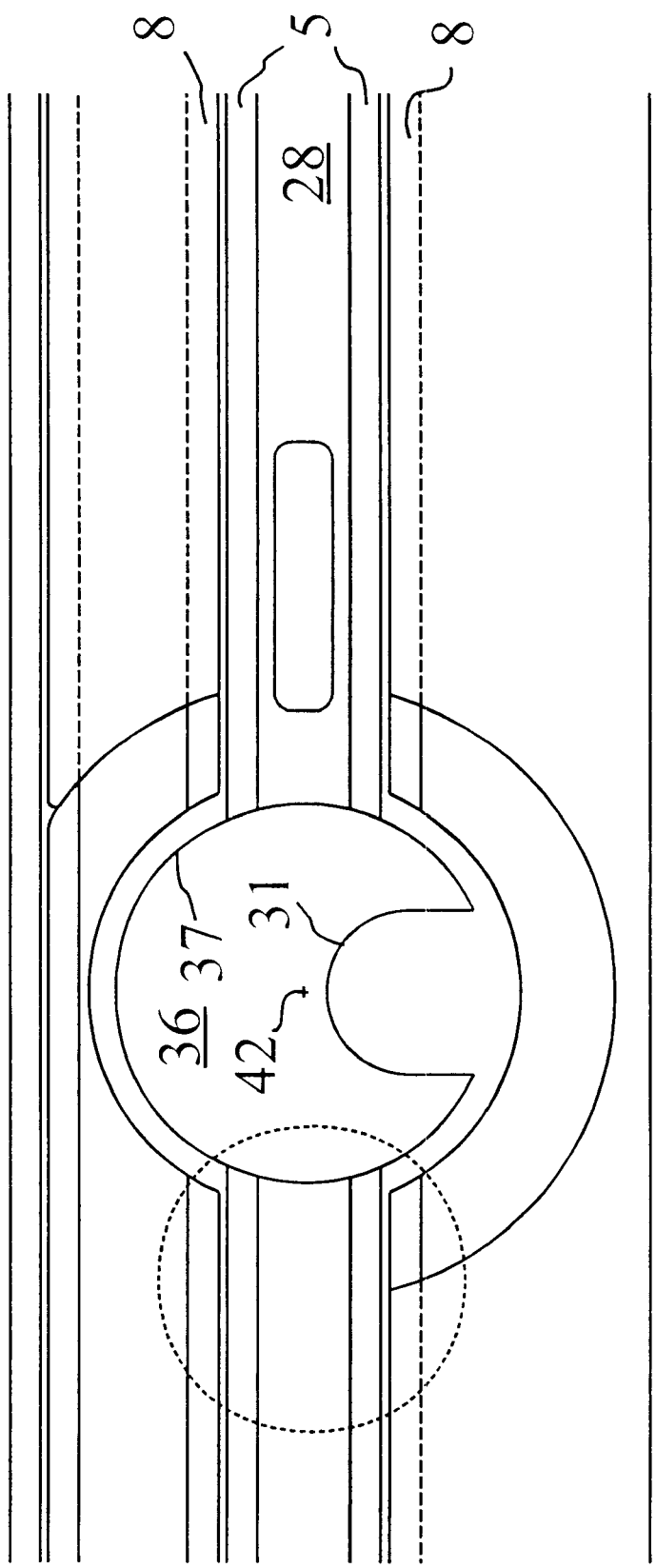

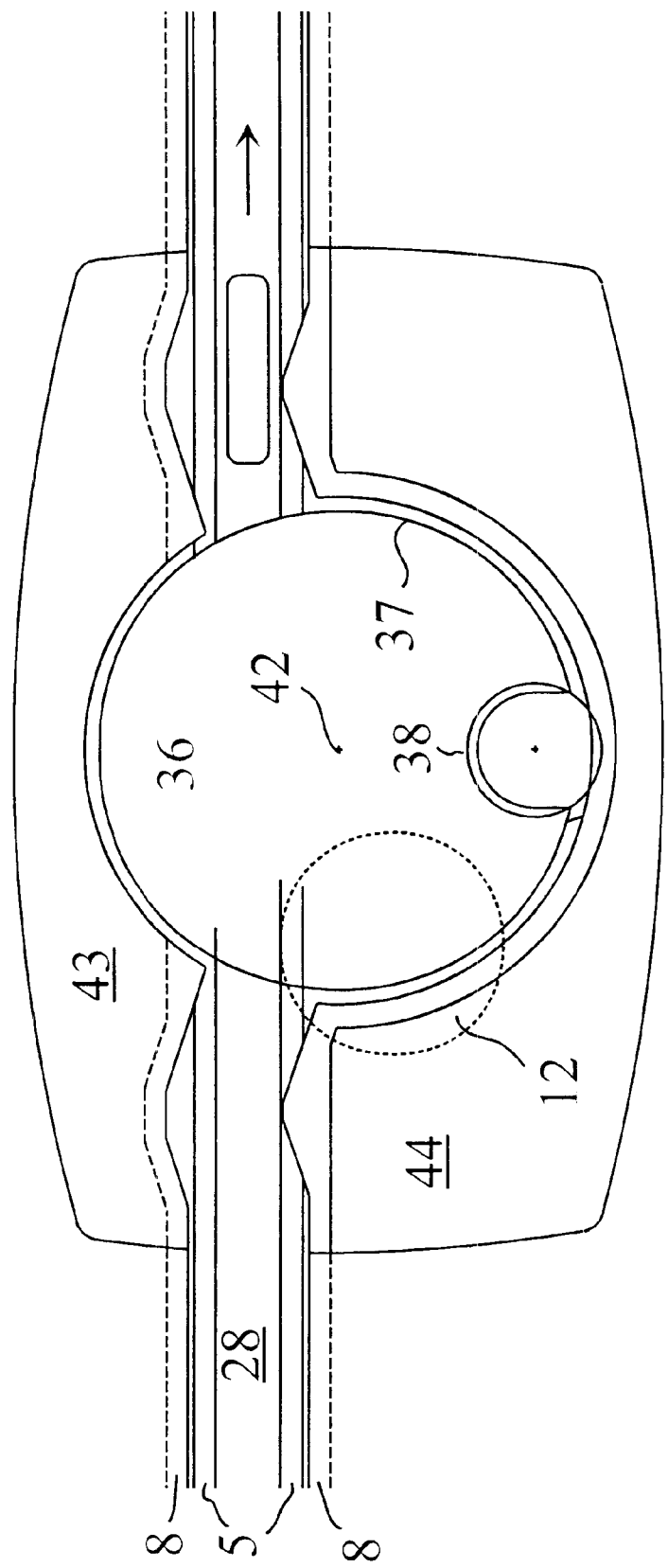

ARRANGEMENT AND METHOD FOR HANDLING TEST TUBES IN A LABORATORY

The present invention relates to an arrangement, according to the preamble to claim 1 for transporting and preferably for monitoring test tubes automatically between the various process stages and equipment in laboratories.

The invention also relates to a method for transporting test tubes.

In analysis laboratories, it is necessary to handle large number of samples and to transport them between different process stages and analysers. The samples are placed in test tubes, which are loaded into and removed from the conveyor racks of centrifuges and analysers, with the samples in one test-tube being distributed between others and the test tubes being finally removed and disposed of. The transport and handling of test tubes has been largely carried manually, but various automatic handling systems are increasing in laboratories, due to the increase in the number of samples and the efficiency of analysers. The basic requirements for an automatic conveyor system are the reliable and undamaged handling of test-tubes and the reliable monitoring of the samples in the system. Reliable handling is usually implemented by placing the test tube in a separate transport base, which is guided as it is moved by a conveyor belt along a mechanically delimited track. The position of the test tubes within the system is monitored with the aid of barcodes and code readers. Publication U.S. Pat. No. 5,605,218 discloses a conveyor track, in which the transport base is moved in a U-shaped groove with conveyor bands running in its comers. The bands have a circular cross-section and are arranged to run as parallel continuous loops. The round bands can be arranged to run along complicated tracks, allowing them to be used to create various routes for the movement of the transport bases. The transport bases can be moved from one track to another, by means of cross-track pushers. In this solution, a single conveyor-loop pair forms part of one track, which must be designed in the shape of the desired route, so that the completed track can only be altered by entirely reconstructing a single track section. The devices for transferring the transport bases from one track section to another are extremely simple and can be used only to move the bases between two parallel conveyor sections and only in one direction. Thus, this solution is only suitable for applications, in which there is little variation in the route of the samples, and in which the samples are handled in a fairly precise order. It is difficult to alter or extend a completed track, as this requires entire track sections to be replaced. U.S. Pat. No. 5,657,856 discloses a solution, in which a conveyor system similar to that described above can be made partly modular, with the system formed by two round bands forming a single module. The modules are connected by means of plate belts synchronizing the movement of the round belts. The connecting units are quite complex and are unnecessarily expensive, because they also include electric motors to drive the belts.

Canadian patent application 2,216,052 discloses a system for handling test tubes containing bio-samples. In this solution, there are at least two transportation lanes, along which the test tubes, located in transport bases, are moved. The transportation lanes comprise plate belts that move the bases, with guide walls and partitions at the sides of the belt, to divide the belt in the centre into lanes. Each test tube has a barcode attached, which permits monitoring of its location and examination of the operations to be performed on it. The apparatus includes the necessary number of barcode-reader stations to read the barcode. As the barcode's position on the surface of the test tube cannot be known in advance at the reading station, each station has devices to rotate the transport base with the test tube, so the code can be read. This makes the reading station quite complicated and test-tube identification time consuming, which can be a nuisance, if the transportation system capacity must be large, with correspondingly only a short time to process each sample at a each station.

As different kinds of operations, requiring different processing times, are performed on the samples in the transportation system, the system must have devices for altering the order of travel of the samples. In the system referred to above, this takes place by forming two openings, through which the transport bases can be transferred, in the partition dividing the conveyor line. The openings are arranged in connection with an inspection station. In the direction of travel of the transport bases, each parallel lane has first a distribution device for gripping a transport base, followed by a transfer device for moving the transport base through the opening, from one lane to another. The transfer devices are located at the openings, which are on either side of the inspection station's barcode reader. The distribution device can grip one transport base at a time and prevent the others from moving along the lane, so that an individual transport base can be separated from the rest of the flow. The separated transport base can now be guided to a code-reading station on the other lane or to a parallel lane. This arrangement mainly allows the transport bases to be directed to continue forwards along the same lane, or to transfer them to a parallel bypass or waiting lane. Transport bases can only be transferred between two parallel lanes, but not away from the conveyor, for example, to another crossing conveyor. The system also does not know what sample is coming to the distribution device, so that samples must first be guided to a separate code-reading station, so that they can be directed forwards. As the same reader head is used to identify samples on both lanes, the number of samples the station can handle is limited. Sample identification and direction requires separate distribution devices to break the flow of movement and separate devices to guide samples between the two lanes, but even then samples can only be transferred between two parallel lanes.

The invention is intended to eliminate the defects of the state of the art disclosed above and for this purpose create an entirely new type of arrangement for automatically handling samples, which allows samples to be transferred, in a controlled manner in a single control point connected to the conveyor, if required to several alternative stations, for example, after a delay forwards on the conveyor, to a sample-processing station, to an analyser, or to test-tube filling or removal. A preferred embodiment of the invention is intended to create an arrangement, which uses the sample transport bases to rapidly identify a sample arriving at the control point and decide the sample's route from the control point to the next transfer or processing stage.

The invention is based on a control station being arranged in connection with at least one conveyor and including at least a handling member, with a grip for gripping a transport base and transferring the base transversely to the direction of movement of the conveyor, to take the transport base from the first processing point, for example, the conveyor, to the following processing point, and devices for preventing the next transport base from entering the control station during the transfer.

The transport bases in one preferred embodiment of the invention incorporate an RF memory circuit, in which data can be entered and read without contact in, for example, a control station, which can then decide which processing point to transfer the transport base to.

According to a second preferred embodiment, a processing device is arranged in connection with the conveyor feeding transport bases to the control station and includes at least one recess to receive a transport base and a surface shaped as a segment of a circle, which is arranged to move into the path of the conveyor, preventing the next base from entering the control station, until the previous base has been fully processed.

According to a further preferred embodiment, at least one conveyor in the arrangement comprises a conveyor-base path bounded by track-like side walls and at least one, preferably two parallel belts set vertically, on the edge surfaces of which the transport bases are arranged to move.

More specifically, the arrangement according to the invention is characterized by what is stated in the characterizing section of claim 1.

The method according to the invention for transporting and monitoring test tubes is, in turn, characterized by what is stated in the characterizing section of claim 11.

Considerable advantages are gained with the aid of the invention.

The invention allows test tubes to be transferred rapidly and reliably between various processing devices, such as conveyor modules, filling and removal stations, operation stations, analysers, and processing equipment. Samples coming to a control station can be transferred to several alternative stations, to the next process stage or to move forwards. A control station can even be used to transfer transport bases to a crossing conveyor or to a conveyor moving in a direction otherwise different to that of the conveyor bringing the transport bases to the control station. If an RF memory circuit is used to identify transport bases and samples, identification data can be read rapidly and, as the small read/write sensor can be located almost anywhere, its location does not restrict the mechanical design of the system. As the position of the transport base does not affect the data entry or reading, the base need not be rotated or otherwise positioned to read the identification data. Thus the handling of the transport bases, at control stations or elsewhere the data in the RF memory circuit must be processed, is extremely rapid. The handling devices of the control station can grip the transport base firmly and the transport base can be moved onto a fixed base, for example, while working with a pipette, eliminating test-tube vibration due to conveyor-belt movement. The handling devices can also be used to centre the test tube reliably in a desired position.

The conveyor components of the arrangement comprise various conveyor modules, in which there is a track preferably delimited by rail-like walls, on the bottom of which two toothed belts are set vertically. The transport bases are arranged to travel on top of the edges of these belts. As the vertically set thin toothed or other belts can turn through a small radius at the ends of the modules, the ends of the belts of sequential modules can come close together and require no other devices to ensure that the transport base will move reliably to the next module. The belts are also in an upright position, so that the outer edges of their turning circles lie next to each other and can almost touch each other, so that the belt does not curve under the conveyor surface, which would form a gap in the conveyor track surface between the belts, corresponding to the turning radius. Modules made in this way can be easily joined as different systems, as they need only be connected to each other structurally and require no connector pieces between them synchronizing movement or containing operating devices. The transport bases are preferably symmetrical around their axis of rotation, so that they need not be in a specific position on the conveyor, but can be freely rotated around their vertical axes by the conveyor or other handling devices. Because reading of the identification data also does not demand a particular position, the bases can be easily controlled. The shape of the transport base fits the shape of the edges of the track in such a way that the bases travel in a controlled manner along the track and are not able to tilt or fall.

The entire arrangement according to the invention permits the formation of a complexly-shaped and easily varied handling system. Damage to a single module will not affect the operation of the rest of the system, so that the entire system will be operational once again after replacement of the module. It is also easy to detach modules for maintenance, replacing them with spare modules for the time required, thus interrupting operation only for a short time. The solution according to the invention is especially advantageous in possible contamination situations, such as blood samples or similar coming in contact with the conveyor system. Normally the conveyor belts will only spread the contents of a sample over the area of a single module, unlike in the arrangement of publication CA 2,216,052, for example, in which the belts extend, through contact with each other, over the area of the whole system, allowing a sample to spread over a very large area and, requiring, in the worst case, the entire system to be cleaned. Sample control is extremely flexible, because both identification and transfer of the transport bases are rapid and certain. Samples can be fed into the system irrespective of the capacities of the individual devices at that moment, because samples can be taken from the sample flow to the processing and analysis equipment according to how many samples the equipment can handle. Waiting samples can circulate freely in the system and bypass the processing points, or be switched to separate buffer modules to wait. As the identification data of the transport base and sample are read whenever the base is handled, the system control unit need not continuously know where individual bases are in the moving flow, which facilitates system control and programming. The track is preferably enclosed, samples being placed on it and removed from it only through the reading points, so what samples are on the track and being processed by the various devices is always known.

In the following, the invention is examined with the aid of examples and with reference to the accompanying drawings.

FIGS. 3–5 show various control stations according to the invention.

Figure 1:
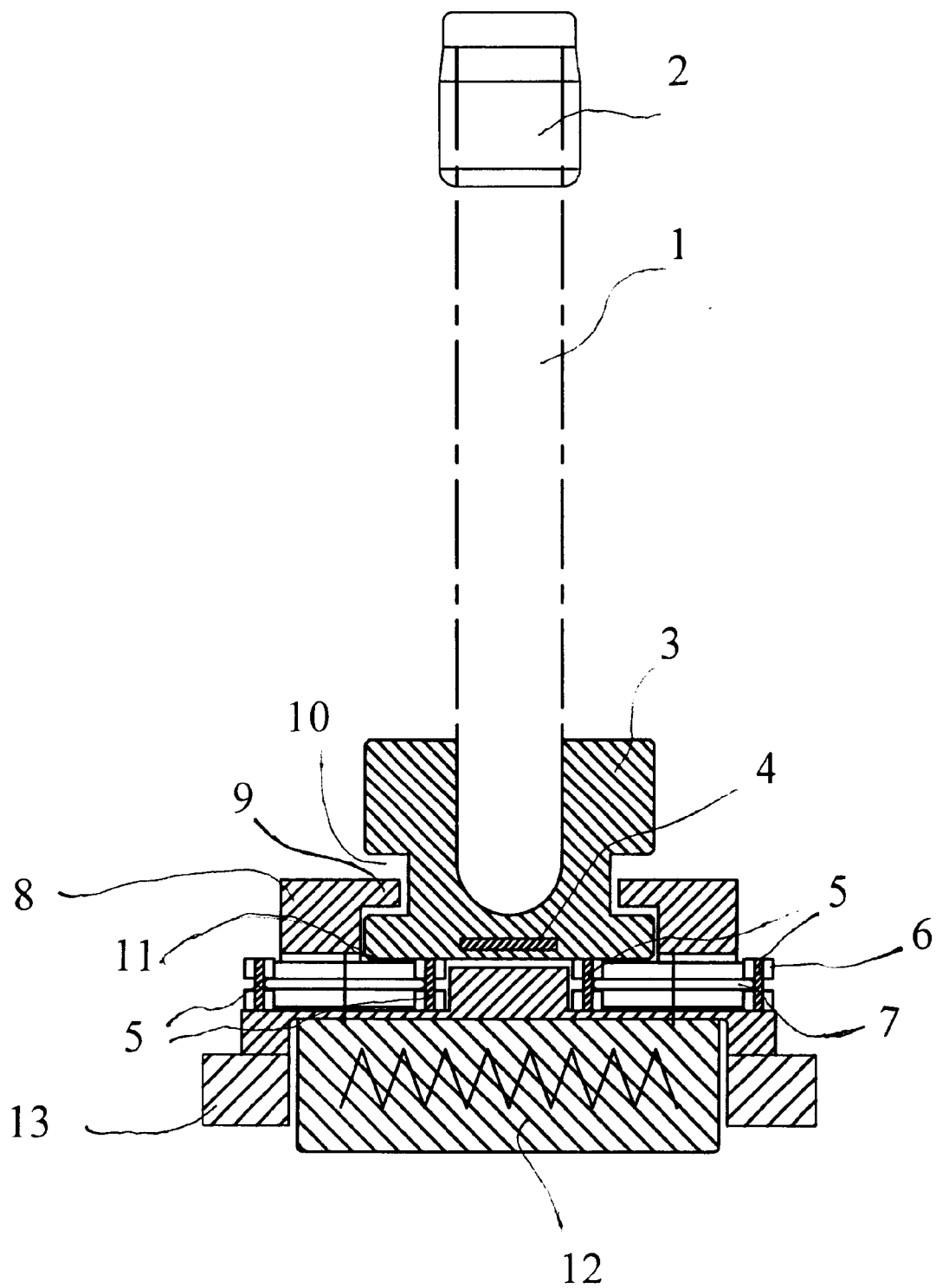
FIG. 1 shows a cross-section of one transport base according to the invention on one conveyor according to the invention.

In FIG. 1, test tube 1 fits into a recess formed in transport base 3. Transport base 3 must have suitable retaining members to receive and support, for example, 5, 7, and 10 ml test tubes on base 3. The retaining members can be implemented, for example, using flexible tongues or similar. Test tube 1 is usually closed by a cork 2. Transport base 3 is a rotationally symmetrical piece, with a groove 10 and a flat bottom surface 11. Base 3 is arranged to travel on a conveyor, which is constructed on a frame 13. Frame 13 is preferably of aluminium profile or sheet, with a plastic movement base 8 fitted on top of it and delimiting the track of transport base 3. Frame 13 forms a support for movement base 8. The track edges are bounded by rails, with flanges 9 in their upper edges, which fit into groove 10 in the transport base and lock transport base 3 vertically to the track by their closed shape. Naturally, they must fit sufficiently loosely to allow the base to travel freely in the direction of the conveyor.

Conveyor movement base 8 has two grooves in the track, parallel to the direction of movement, into which toothed belt 5 fits transversely. Thus each track has two belts 5 parallel to each other. Belt 5 are arranged as continuous loops, with one half of the belt travelling outside the track, the pair of belts 5 moving in the same direction as the track and the return movement taking place outside the track. Belts 5 are driven and guided by belt pulleys 6. The axles of belt pulleys 6 run vertically and the pulleys have a guide flange 7 fitting into a groove in belts 5. This prevents belt 5 from both deflecting downwards at pulley 6 due to the load or from rising. The belts can be driven from any one of the pulleys 6, using, for example, a shaft-drive motor or some other operating device. Belts 5 are arranged so that their transverse axis of the belt is vertical, i.e. their narrow edges point upwards and correspondingly downwards. The upper edges of belts 5 extend slightly above the edge of the groove in movement base 8, while transport base 3 is arranged to travel supported on the upper edges of belts 5. The lower edges of belts 5 are supported on the bottom surface of the grooves in movement base 8, in addition to the guide flanges 7. The belts are preferably toothed belts, because they allow the belt to be driven by sprockets and can bend easily around their transverse axis, so that they can be bent to a small radius. The teeth of the belt also support the transport base and increase the support surface of the edge of the belt, without increasing the stiffness transversely to the bending radius of the belt.

An RF memory circuit 4, in which the data required to process and identify the sample can be recorded with the aid of RF antenna 12, is fitted to transport base 3. For example, chip 4 can be either moulded inside the transport base, which is made from plastic, or glued to it. RF antenna 12 is very small and can read and write to chip 4 at a distance, so that antennae can be easily placed in the desired locations on the conveyor track.

Figure 2:
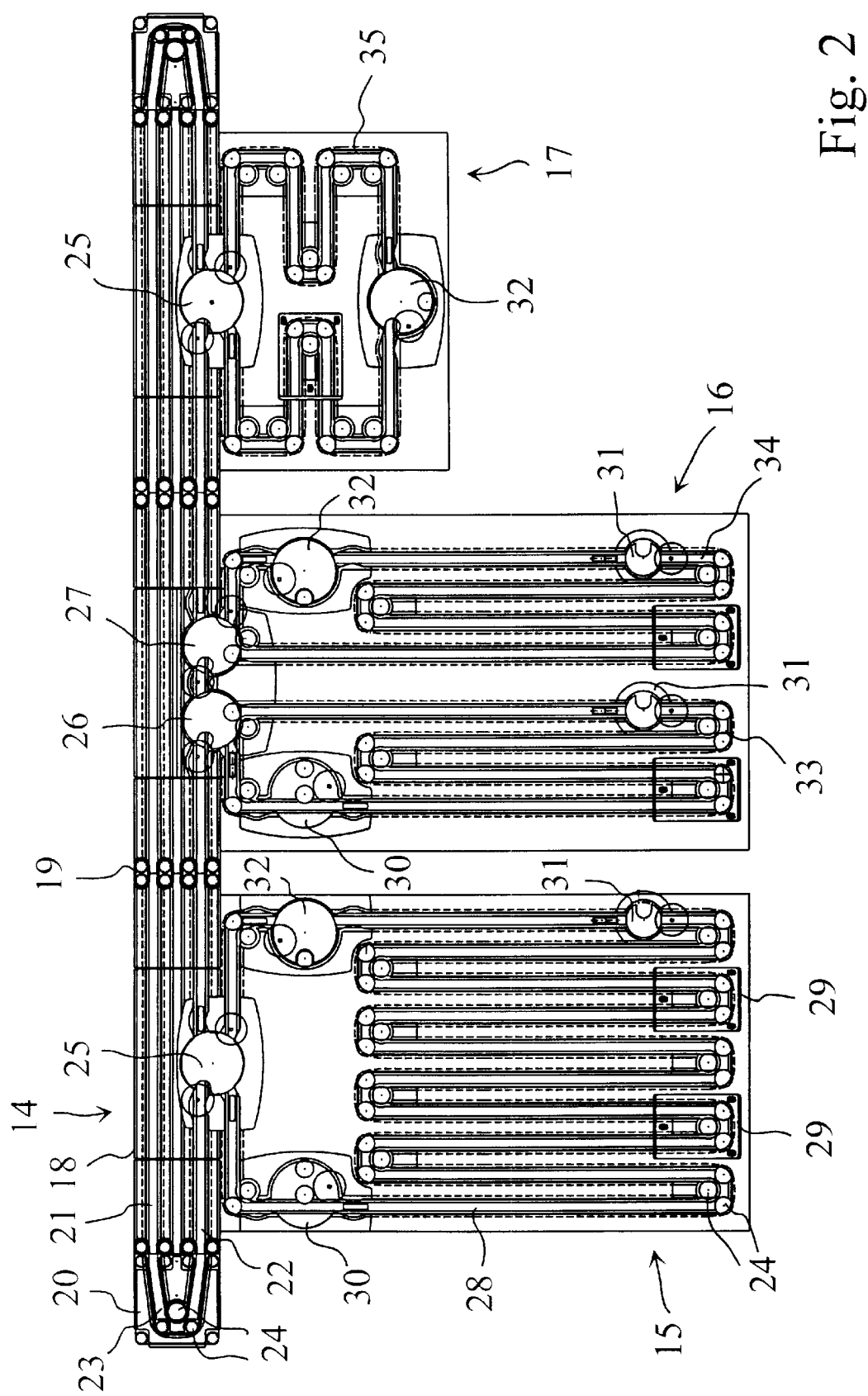
FIG. 2 shows one conveyor system implemented according to the invention.

FIG. 2 shows one conveyor system implemented using the invention. This system comprises four main modules, i.e. cells, which are a large-capacity storage cell 15, a feed/removal buffer 16, a bypass cell 17, and a connecting conveyor 14. The conveyor comprises conveyor modules 18 of a predefined size, each of which has two tracks 21, 22 moving in opposite directions to each other. Thus, the straight conveyor modules 18 have four belts 5, arranged to travel in loops from one end of the module to the other. At the ends of the modules, there are belt pulleys 6. At the interfaces 19 between modules 18, the modules are simply connected mechanically to each other in such a way that the directions of movement of the tracks remain the same. No kind of operating device is needed at the interfaces to transfer the transport bases over the interfaces, making the connection as simple as possible. At the ends of the conveyor, there are turning modules 20, with a U-shaped track 23. The track of a turning module 20 has two belts similar to those in the straight modules, which are guided along the desired track by pulleys 24. The track of a turning module 20 is formed so that the ends of the track coincide with tracks 21, 22 of the conveyor modules, allowing turning modules 20 to be used to transfer transport bases to the straight conveyor track moving in the opposite direction.

The straight conveyor 14 is connected to the other modules in the system through control stations 25, 26, and 27. The control stations may differ in construction and operation, their operation being disclosed later.

The left-hand side of FIG. 2 shows a storage cell 15 with a long winding conveyor 28, which can hold a large number of transport bases awaiting processing. The conveyor track of the storage cell can be selected freely, because a belt moving in an upright position can be easily arranged to travel along the desired track by means of pulleys 24, while the rails bounding the track can also be easily shaped to suit the desired track. The most compact construction, however, is obtained with parallel one-way track sections connected by 90°-curves. The storage cell described can be formed using two belt loops moving along the desired track in the same way as in the other cells, or else the cells can be assembled from components similar to those in the straight conveyor. As the belts in these special modules will become quite long, tensioning of each belt must be possible. This takes place using simple tensioning pieces 29, on which a pair of pulleys of one belt are mounted adjustably, to allow the pulleys' position to be altered. In the case of the 90°-bends of FIG. 2, tensioning of both belts can be in the same tensioning piece, as the tensioning force for both belts acts outwards from the bend of the curve.

The other modules 16, 17 are constructed in basically the same way as the storage module described above. The purpose of the modules is varied by simply altering the shape of the track of the conveyor and arranging various control stations at the desired locations. There are three control stations in storage module 15, which is connected to the straight conveyor 18 by a fourth control station. Control station 25 connecting storage module 15 and conveyor 18 is a junction station, which is used to control traffic between the storage module 15 and conveyor 18. In storage module 15, the belts circulate anticlockwise, the first control station in the direction of movement being bypass station 30. The next is stopping station 31 and the last is operation station 32.

Feed/removal buffer 16 comprises two separate conveyor tracks 33, 34. Each track has a stopping station 31 to load transport bases onto the conveyor track or remove them from it. In FIG. 2, the conveyor track of module 16 on the left-hand side of the figure is a removal track, comprising both a stopping place 31 and a bypass station 30. The track on the right is a feed track, in which there is an operation station 32. At feed track 34's operation point 32, there is preferably a barcode reader, which reads the test tube's barcode and enters the data required to process the sample into the RF memory circuit of the transport base. After this, the barcode need not be read anywhere else, unless the operation of some external device connected to the system requires this. Feed and removal tracks 34, 33 are connected to the conveyor through junction stations 27, 26. Bypass cell 17 is connected to conveyor 18 through junction 25 and contains a conveyor section 35 forming a short storage section, and a single operation stations.

Figure 3:
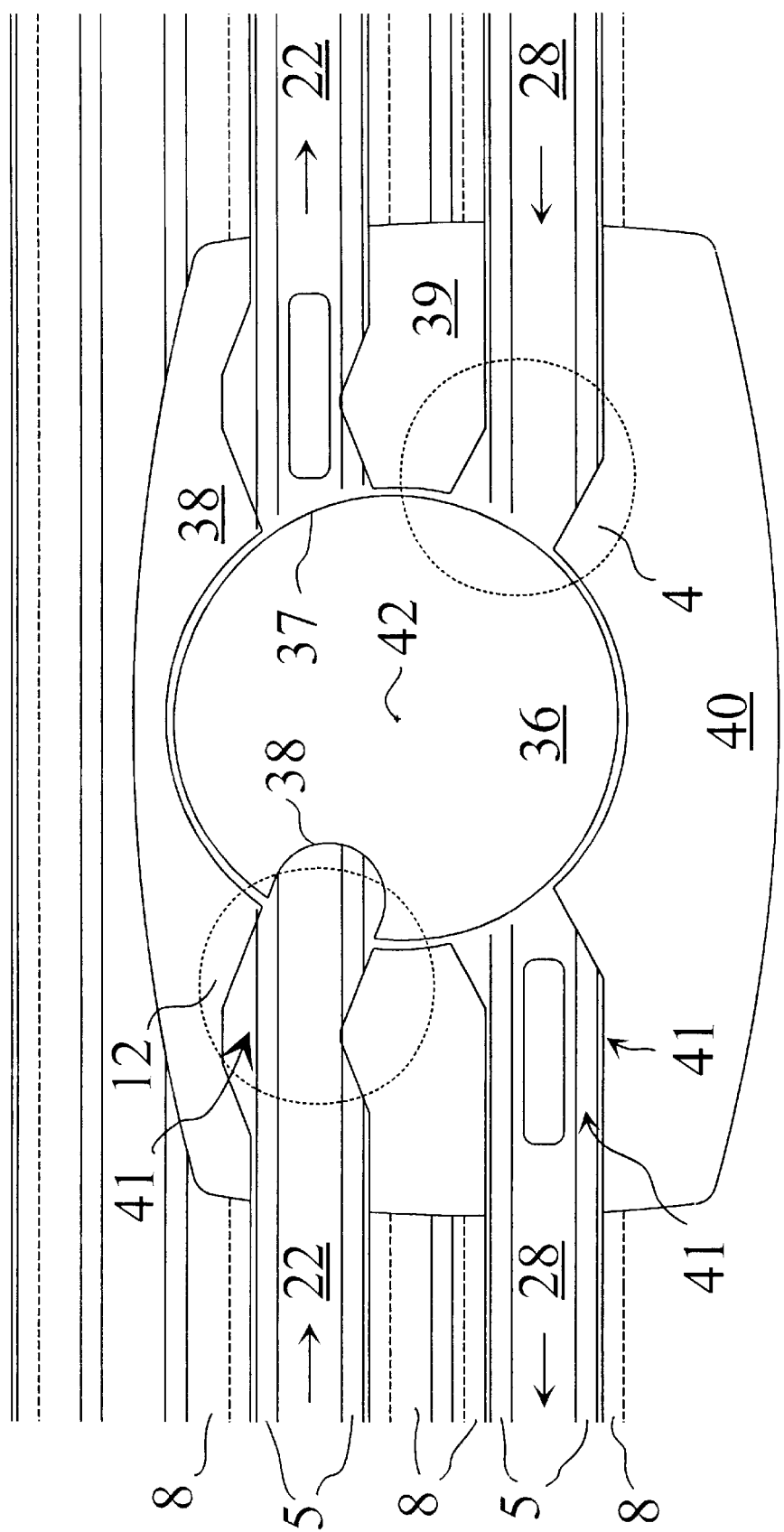

Junction station 25 operates in such a way that a transport base approaches the junction station along the conveyor track. Under the approach track to each junction station there is an RF antenna 12, which identifies the sample by reading the data in the RF memory circuit. If necessary, it updates the data. Guide disc 36 is then positioned so that the circumference 37 of the disc covers the entry opening. After sample identification, grip 38 is moved to the position shown in FIG. 3 and the base moves into grip 38. Now the disc is rotated to move the grip to the opening where the transfer of the sample must continue. At this junction station, a transport base moving on track 22 can be switched either to continue along the same track, or onto parallel track 28, when its direction of travel changes. A base moving on track 28 can be moved similarly. One application for such a junction station 25 is to pick transport bases from conveyor 14 to modules.

Feed/removal module 16 has otherwise similar junction stations, but with conveyor tracks in different directions. As these examples show, the operation of the junction station is not affected by the incoming or outgoing tracks' directions, which can therefore be freely selected as desired.

FIG. 4 shows a stopping station 31. Here handling device 36 rotates around a centre 42 on the centreline of track 28 of the conveyor, so that guide panels are not absolutely essential and the transport bases can travel in a straight path. The recesses required by disc 36 are formed in the edge rails of movement base 8. A transport base arriving at stopping place 31 stops against the circumference of disc 37 and the data in its RF memory circuit are read. Next, the disc is rotated to move the base either to the side of the track or to continue along track 28. At the side of track 28, the transport base can be on an even surface, so that the movement of belts 5 does not vibrate the test tube. If vibration is not detrimental, guide disc 36 can have such a small diameter that the transport base remains partly on top of one belt. Once the transport base has been moved to the side of the track, the desired operations can be performed on the sample. These include placing a sample on or removing it from the transport base, feeding a transport base into or removing it from the system, reading/writing the RF memory circuit, pipeting the sample either over the antenna or at a side station, and holding the movement of the transport bases, for example, for buffering or batching. The operation station in FIG. 5 is otherwise similar to a stopping station, but uses guide panels 43, 44, and an eccentric guide disc to move transport bases clearly to the side of the track for an operation. In this case, the RF antenna is located inside the disc's operating area, allowing sample data to be updated, without taking the transport base onto the conveyor track. Operations similar to those carried out at the stopping station can be carried out at this operation station. At both stations, labelling, barcode reading, corking and cork removal, and contents examination are also possible. If required, samples can also be weighed at this station. Operation station 32 has the advantage that the transport base is clearly removed from the conveyor, so that it is unaffected by the conveyor's motion, making it easier to perform operations requiring space, such as barcode reading.

Bypass station 30, for example that in storage module 15, differs from those above by having a semicircular guide disc. This permits the disc to be turned to a position with a straight track past the station. Of course, a recess must then be formed in the other side of the track, to permit turning. As the edge rail of movement base 8 must then be cut, a guide member that, for example, rises or moves aside during turning must be fitted at the cut, to guide transport bases travelling in a straight line.

A system according to the invention can operate in many different ways. The possible forms of operation of the system of FIG. 2 will next be described, as an example.

Samples can be fed into the system, either by placing them on transport bases already in the system, or adding transport bases with test tubes attached, to the system. Both operations can take place at the feed/removal module's stopping station 31. The transport base moves from this stopping station to an operation station, where the test tube's barcode is read and the necessary data entered in the RF memory circuit. Next, the transport base can either move to the entire conveyor system, or recirculate to wait on feed line 34. Samples are removed similarly, the removal conveyor having free space for transport bases awaiting removal. The removal track has one more bypass station, which can pick out samples for one more processing stage or for data examination. At other stations in other modules, operations take place similarly, i.e. transport bases are guided as required by control stations to an operation, to another track, past an operation point, or are arranged in a queue.

Within the scope of the invention, embodiments of the invention, differing from those disclosed above, can also be envisaged. The above material selections and constructions are only examples of working solutions. It is obvious that any suitable structural materials can be used to build a system and that the form of the constructions can vary. For example, the shape of the transport base and the corresponding guide bounding the track can be chosen freely, provided it creates a sufficiently reliable guide. The transport base can also be envisaged as not being rotationally symmetrical, but it will then be more difficult to guide the base and design the track, as the base must then be made to travel in a specific position, if it is to be successfully handled. The control stations' handling devices can be of any kind, such as rotating cams, but the disc construction disclosed above, rotating around its vertical axis, is simple to implement and extremely reliable in operation. However, the disc may have several grips. Here, an RF memory circuit refers to any recording method, which can be used to record and read data, without physical contact. The test tubes' identification data is usually a barcode, but a system implemented by means of the invention can use any identification system whatever in general use. The system's sensor arrangement, control, and operation can be arranged as desired to suit the requirements of the application, the design of the components being within the scope of the skills of one skilled in the art. The modular track system is preferably enclosed, so that samples can only be put into and removed from the system through the control points, allowing case the system to preserve reliable information on the samples in the system and preventing transport bases with insufficient identification data from moving in the system. Naturally, there may be only a single conveyor belt or more than two conveyor belts in the same track, but a single belt may not necessarily give sufficiently smooth movement to the transport base, while the use of several belts will complicate the construction of the apparatus and will be justified only if the bearing surface between the transport base and the belts must be increased.

What is claimed is:

1. An arrangement for transporting test tubes (1) automatically between different processing stages and equipment in laboratories, which arrangement includes:

at least one transport base (3) for receiving test tubes (1), at least one conveyor for moving the transport bases (3) in the arrangement, at least one processing point on the track (28) of the conveyor, at least one other processing point, and devices (36, 38) for moving the transport base (3) from the first processing point to a second processing point, a control station arranged in connection with the track (28) forming together with the conveyor track (28) at least one processing point, and which control station includes at least a handling device (36) with a grip (38) for gripping a transport base (3) and transferring the base (3) in a direction transverse to the direction of movement of the conveyor track, to take the transport base (3) to the next processing point after the first processing point, and devices (37) to preventing the next transport base (3) from entering the control station (25) during the transfer, the outer perimeter of the handling device being formed at least partially of an arc of a circle and at least one grip for receiving the transport base being arranged on the arc, the grip being formed by forming recess corresponding to the shape of the transport base.

2. An arrangement according to claim 1, wherein it has at least one transport base (3) with an RF memory circuit (4) fitted and at least one RF antenna (12) for entering data in and reading data from the RF memory circuit (4).

3. An arrangement according to claim 1, wherein the circumference (37) of the handling device forms at least part of the arc of a circle and in the arc (37), said at least one grip is arranged, which is created by forming a recess (38) in the arc (37) corresponding to the shape of the outer surface of the transport base.

4. An arrangement according to claim 3, wherein the handling device (36) is arranged to rotate around a vertical axis (42) to one side of the centreline of the conveyor track (28) and at least one conveyor track (28) lies at a tangent to the handling device.

5. An arrangement according to claim 4, wherein the track of the grip (38) has at least one processing point, which is entirely outside the track (28) of the conveyor.

6. An arrangement according to claim 4, wherein beneath the track (28) of the conveyor, there is an RF antenna located before the handling device (36), to identify the transport bases arriving at the control station.

7. An arrangement according to claim 4, wherein beneath the path of the grip (38) of the handling device (36), there is an RF antenna located to the side of the conveyor track (28), to process the data in a RF memory circuit (4) of a transport base (3), before the base (3) moves to the conveyor.

8. An arrangement according to claim 1, wherein the transport bases are rotationally symmetrical.

9. An arrangement according to claim 1, which includes at least one conveyor comprising a track (28) and at least one belt (5) for moving transport bases (3) along the track (28), wherein the track (28) is bounded by sides and at least one belt (5) is arranged to travel in an upright position within the area of the track, so that the edge of the belt (5) is on the track and can carry a transport base (3).

10. An arrangement according to claim 9, wherein there is a groove in at least one belt (5) and at least one pulley (6) guiding the belt (5) has a flange (7) that fits into the groove, to guide the belt into an upright position.

11. A method for transporting test tubes automatically between various process stages and equipment in laboratories, in which method:

the test tubes (1) are set on transport bases (3) for transportation in the conveyor system, the identification data of the test tube (1) is read to identify the sample, the transport bases (3) are moved in the transportation system with the aid of conveyors (15–18), and at least one transport base (3) is taken to at least one operation station (32) for an operation to be carried out on the test tube (1) or sample, the data necessary to transfer the sample within the system, on the basis of the identification data of the sample, is entered in a recording device (4), able to be read without physical contact, belonging to the transport base (3), the transport base (3) is handled at least one control station (25), which comprises at least one handling point and the conveyor track (28), and which control station includes at least one handling device (36), in which there is a grip (38) by means of which the transport base (3) is gripped and moved in a direction transverse to the direction of travel of the conveyor track, to take the transport base (3) from the first processing point to the following processing point, and devices (37) by means of which the next transport base (3) is prevented from entering the control station (25) during the transfer, the outer perimeter of the handling device being formed at least partially of an arc of a circle and at least one grip for receiving a transport base being arranged on the arc, the grip being formed by forming a recess corresponding to the shape of a transport base, and the data in at least the recording device in the transport base (3) is read at the control station during handling.

* * * * *